United States Patent [19]

Horwitz

[11] 4,123,660
[45] Oct. 31, 1978

[54] OPTICAL ALIGNMENT APPARATUS FOR TELETHERAPY MACHINE OR THE LIKE

[75] Inventor: Norman H. Horwitz, West Bloomfield, Mich.

[73] Assignee: William Beaumont Hospital, Royal Oak, Mich.

[21] Appl. No.: 770,558

[22] Filed: Feb. 22, 1977

[51] Int. Cl.$^2$ ............... G01B 11/26; G01N 21/00; G01N 23/00
[52] U.S. Cl. .................. 250/491; 350/81; 356/172
[58] Field of Search ............... 250/491; 356/172, 153, 356/150, 138; 350/81

[56] References Cited

U.S. PATENT DOCUMENTS

| | | | |
|---|---|---|---|
| 1,204,694 | 11/1916 | Schaff | 356/138 |
| 2,774,275 | 12/1956 | Keller | 356/138 |
| 2,849,911 | 9/1958 | Brunson | 356/138 |
| 3,588,249 | 6/1971 | Studebaker | 356/172 |
| 3,941,480 | 3/1976 | Webster et al. | 356/172 |

OTHER PUBLICATIONS

Rue, Arthur K., "Calibration of Precision Gimbaled Pointing Systems," *IEEE Transactions on Aerospace and Electronic Systems*, vol. AES-6, No. 5, Sep. 1970, pp. 697–701.

*Primary Examiner*—Alfred E. Smith
*Assistant Examiner*—T. N. Grigsby

*Attorney, Agent, or Firm*—Cullen, Sloman, Cantor, Grauer, Scott & Rutherford

[57] ABSTRACT

In conjunction with a linear accelerator or a cobalt-60 teletherapy machine disposed in a room having a head mounted for rotation about a horizontal epicenter axis, and wherein the head is adapted to direct a high energy beam at right angles to and intersecting said axis at an isocenter, there is provided right-angularly related opposed pairs of lasers whose beams are focused upon said isocenter. This is to assure that when an isolated area of a patient's body to be treated is located at said isocenter, with the laser beams impinging upon said isolated area, that the high energy beams will at all times pass into said isolated area, as the radiation head is rotated up to 360 degrees about said epicenter axis. The present laser alignment fixture includes a support base adjustably mounted upon a universally adjustable patient platform. A turntable on said support base has a telescope mount with top, bottom and side walls and a longitudinal bore. A telescope with a longitudinal axis is nested in said bore and on adjustment of said platform, its axis is adapted for alignment with the epicenter axis. Mirrors are mounted on each of the orthogonal walls of the telescope mount with their axes coplanar and passing through the telescope longitudinal axis. The mirrors reflect the laser beams back to the respective laser in registry with its beam, when the lasers are correctly focused upon said isocenter.

27 Claims, 11 Drawing Figures

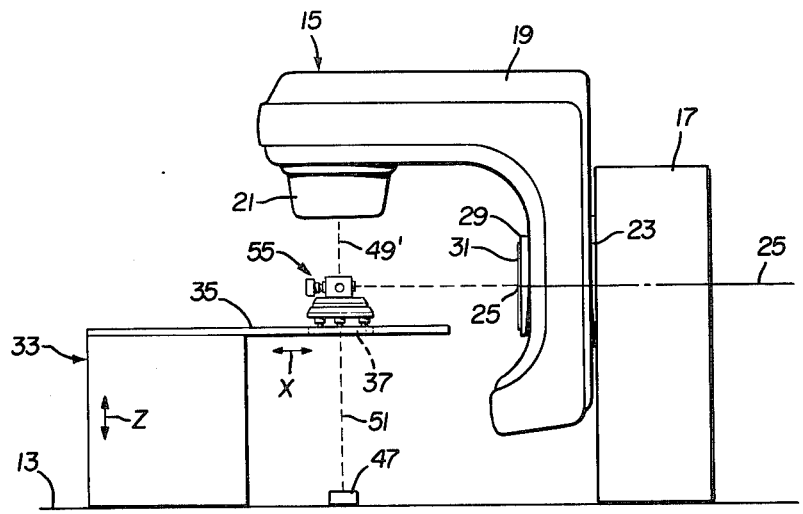
FIG. 2
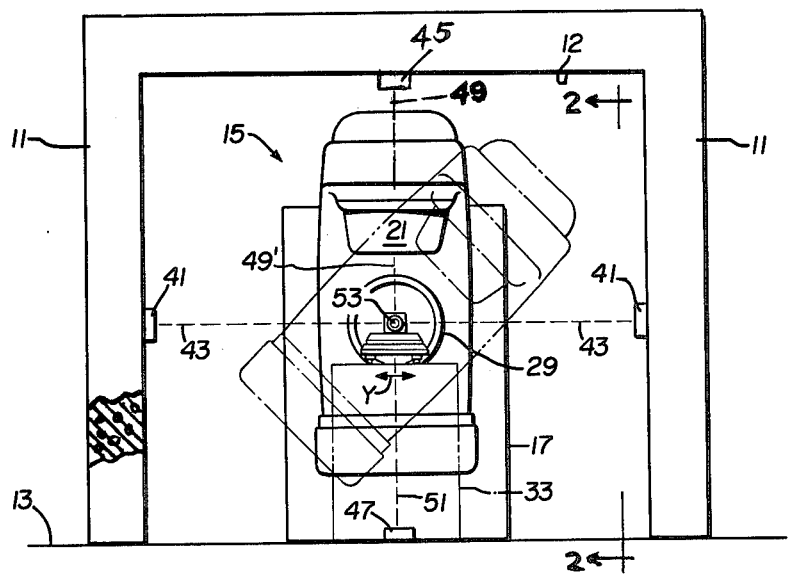
FIG. 1
FIG. 9
FIG. 11
FIG. 10

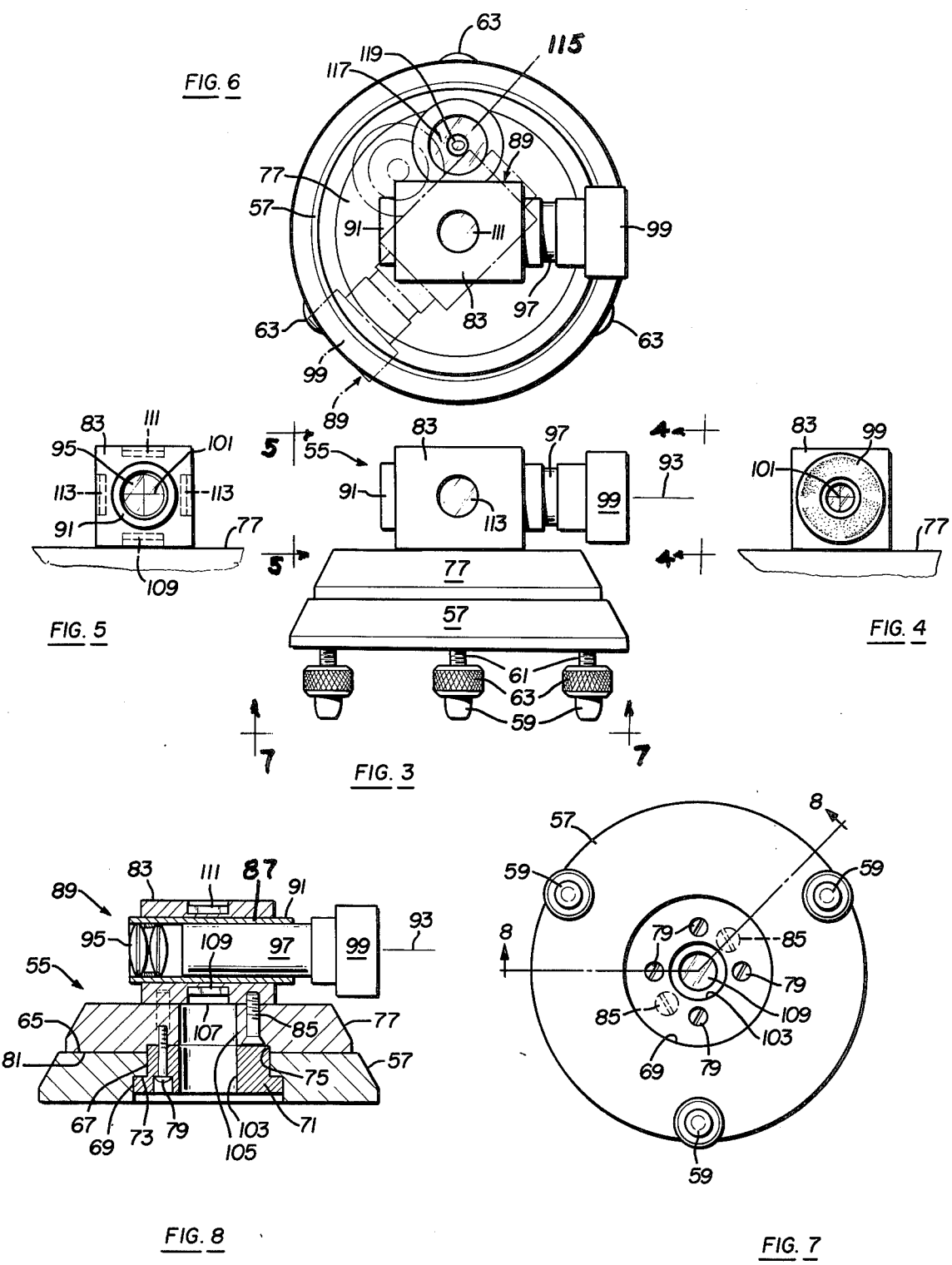

OPTICAL ALIGNMENT APPARATUS FOR TELETHERAPY MACHINE OR THE LIKE

BACKGROUND OF THE INVENTION

It is of utmost importance and an absolute requirement that the lasers and their corresponding beams are correctly focused so as to register with and to intersect the isocenter which corresponds to the point at which the high energy beams from the radiation head intersect the epicenter axis of rotation. It is the correct and accurate focusing of the laser beams, or light beams, upon said isocenter which will assure that throughout rotation of the accelerator high energy head throughout 360° about the aforesaid epicenter axis, that the high energy rays will impinge upon the isolated area of the patient to be treated when said isolated area is likewise located at said isocenter.

Accordingly, when the patient in a horizontal position rests upon the universally adjustable platform of the patient couch adjacent and spaced from the teletherapy head, and the isolated area to be treated has impinged thereon the respective rays of at least three of the four laser beams, it is then assured that the high energy beam from said head will impinge upon only said isolated area regardless of its position of rotation with respect to the epicenter axis.

It is important, therefore, that the laser beams be focused and that they are, at all times, directed to and intersect said isocenter. Since these lasers are adjustable, it is often possible that they may be accidentally moved out of adjustment and thus, would give an incorrect registry and their beams would no longer be in focus with the above-described isocenter. The problem, therefore, is to have assurance that the lasers or other light sources are so adjusted for use in conjunction with the linear accelerator that the beams are correctly and accurately focused upon said isocenter.

SUMMARY OF THE INVENTION

It is an object of the present invention to provide a laser alignment fixture to thus provide a visible means of predetermining that the respective laser beams are accurately focused upon the isocenter in order that the linear accelerator and its head will deliver high energy beams at said isocenter when the isolated area of a patient to be treated is positioned at said isocenter.

It is another object to provide a laser alignment fixture for use in conjunction with a teletherapy machine which has a head supporting gantry mounted for rotation upon an epicenter axis and wherein, the head is adapted to direct a radial high energy beam at right angles to and intersect the epicenter axis at the isocenter. The present alignment fixture includes a telescope having a longitudinal axis which, upon suitable adjustment of the support for the alignment fixture, permits visual alignment of the telescope longitudinal axis with the epicenter axis. A series of right-angularly related mirrors are mounted upon the telescope in such a manner that the respective axes of the mirrors are coplaner and pass through the said longitudinal axis whereby laser beams are correctly focused upon said isocenter to assure high energy treatment only at the designated area of the patient's body.

The present laser alignment fixture is adapted for use in conjunction with a teletherapy machine having a head mounted for rotation about a longitudinal epicenter axis and with the head adapted to direct radial high energy beams at right angles to and intersecting said epicenter axis at an isocenter. Right-angularly related pairs of opposed lasers are mounted upon a corresponding pair of room walls which enclose the machine, the floor of the room, at a point above the epicenter axis, either from the ceiling or from the linear accelerator head with the respective laser beams lying in a single plane extending at right angles to the epicenter axis and with the respective laser beams intersecting the isocenter. The present laser alignment fixture includes a support base which is normally mounted upon a window forming a part of a universally adjustable platform for a patient couch, normally spaced from the head of said machine. The turntable on said support base mounts a telescope, whose cross hairs, on suitable vertical adjustment of the telescope, are adapted to align with the epicenter axis.

A series of right-angularly related mirrors are mounted upon each of the telescope mount walls so that their central axes pass through the longitudinal axis of the telescope, the said mirrors being spaced from and opposed to the corresponding lasers. Accordingly, when the lasers are correctly adjusted so that the respective laser beams impinge on said isocenter, the respective reflected beams from the corresponding mirrors will coincide visually with the corresponding laser beam.

These and other objects will be seen from the following specification and claims in conjunction with the appended drawings.

THE DRAWINGS

FIG. 1 is an end elevational view of a teletherapy machine with rotative head supporting gantry mounted and disposed within a room with shielded walls, one broken away and sectioned for illustration, and including a universally adjustable patient support platform and couch normally spaced from the head of said machine.

FIG. 2 is a side elevational view of the machine and platform taken in the direction of arrows 2—2 of FIG. 1.

FIG. 3 is a side elevational view of the present laser alignment fixture.

FIG. 4 is a fragmentary end view taken in the direction of arrows 4—4 of FIG. 3.

FIG. 5 is a fragmentary end view taken in the direction of arrows 5—5 of FIG. 3.

FIG. 6 is a plan view thereof.

FIG. 7 is a bottom plan view thereof taken in the direction of arrows 7—7 of FIG. 3.

FIG. 8 is a vertical section of the alignment fixture shown in FIG. 3 with the adjustable legs omitted, taken in the direction of arrows 8—8 of FIG. 7.

FIG. 9 is a fragmentary schematic plan view illustrating the side wall lasers and their beams focused upon the alignment fixture side mirrors, said Figure being on the sheet of drawings which includes FIG. 1.

FIG. 10 is a similar schematic and fragmentary view illustrating the reflected laser beams when they are out of focus with respect to said mirrors.

FIG. 11 is a fragmentary elevational view illustrating the universal adjustment of a laser upon a room wall.

It will be understood that the above drawings illustrate merely a preferred embodiment of the invention, and that other embodiments are contemplated within the scope of the claims hereafter set forth.

DETAILED DESCRIPTION OF THE INVENTION

Referring to the drawings, FIG. 1, there is shown a room whose walls are shielded against the transmission of high energy radiation and which include side walls 11, a ceiling 12 and a floor 13 and within which is positioned and enclosed a high energy teletherapy machine 15. Said machine has a gantry 19, in the preferred embodiment of L shape, mounting the radially directed head 21 of a conventional construction and which includes internal mechanism for directing high energy rays radially inward, such as cobalt rays, X-rays or gamma rays used for the therapeutic treatment of patients.

The head mounting gantry 19 is rotatably supported and journalled at 23, FIG. 2, upon the upright stand 17 within said room and has the longitudinally disposed axis of rotation defined as epicenter axis 25. The stand includes conventional power and control mechanism with remote controls for rotating the gantry 19 and the connected head 21 throughout 360° about the epicenter axis. Said gantry includes upon its inner face and coaxial of said epicenter axis, circular dial 29 with peripheral calibrations from 0° to 360° for rotation about a fixed upright pointer 31. This provides an exact indication of the angle of rotation of said gantry with respect to the upright position shown in FIG. 2. This is a conventional construction.

Within the room upon the floor 13 there is provided a treatment couch 33 having a top platform 35 which is universally adjustable in three directions as designated by the arrows X, Y and Z of FIGS. 1 and 2. The platform includes a transparent window 37 intermediate its ends to permit the passage of a laser beam therethrough.

As further conventional construction, mounted upon a pair of opposed walls 11 are the corresponding lasers 41 whose beams are designated at 43. An additional pair of lasers 45 and 47 are arranged in opposed relation upon the ceiling and floor, whose corresponding beams 49 and 51 are shown schematically in FIG. 1.

When the respective lasers 41, 45 and 47 are correctly adjusted, their corresponding beams will lie in a single upright plane which extends at right angles to the epicenter axis 25. Said beams will intersect the epicenter axis at the isocenter designated at 53, FIG. 1.

In the use of the foregoing apparatus, lasers have been provided at 41, 45 and 47 for providing the respective focusing beams. It is understood that any other light source could be provided which will provide a non-expanding type of focusing beam such as the beams schematically shown at 43, 49 and 51, FIG. 1.

As schematically shown in FIG. 11, the present lasers include the universally adjustable mounting 121 by which the corresponding beams are angularly and linearly adjusted. The corresponding beams are adjusted so that the respective laser beams will directly impinge upon the epicenter axis 25 at a point hereafter referred to as the isocenter 53.

The teletherapy machine 15 and the head 21, direct a high energy therapeutic beam, whether it be cobalt rays, X-rays or gamma rays or any other therapeutic ray. The function of the machine is to direct those rays radially inward, as shown schematically in FIG. 2, so that the rays impinge upon and intersect the epicenter axis 25 at a point referred to as the isocenter 53, FIG. 1. If it is determined that the high energy beam is so directed with respect to an isolated or defined area of the patient's body to be treated, then it is assured that throughout rotation of the head supporting gantry 19 throughout 360° about said epicenter axis 25, that all said therapeutic high energy rays will impinge only upon the designated area of the patient.

It, therefore, is the objective of the therapist that the patient normally in a prone or supine position upon the platform 35 be so positioned with respect to the axes X, Y and Z FIGS. 1 and 2, that the designated area to be treated be positioned that the radially directed high energy beam will engage only that designated area.

As a common practice, some means is required for assuring that the designated area of the patient's body is correctly located so that said designated area will, in effect, coincide with or register with the isocenter 53.

To accomplish this result, the lasers 41, 45 and 47 are preset and adjusted so that their corresponding beams 43, 49 and 51 are directed radially inward, not only within a single upright plane which passes at right angles to the epicenter axis but, wherein all of the rays intersect the isocenter 53. Once it is known that the rays so intersect the isocenter, then by adjustment of the platform 35 with the patient thereon, the designated portion of the patient's body may be universally adjusted so that at least three out of the four rays 43, 49 and 51 will impinge upon the designated area for treatment. Therefore, assuming that the lasers are correctly adjusted and the rays, thus, impinge upon the marked area of the patient, then it will be guaranteed that the high energy beam, FIG. 2, from the teletherapy machine head 21 will be applied only to that designated area.

While lasers are shown at 41, it is contemplated as equivalent that any other light beam source may be employed which is non-expanding in character and which will provide the focusing rays 43, 49 and 51. The preferred embodiment shows the lasers 41, 45 and 47 for generating the laser beams 43, 49 and 51.

Each of the respective lasers has a universal mounting such as shown at 121, FIG. 11, for angularly and linearly adjusting the lasers so that the respective beams may be focused upon the isocenter 53.

LASER ALIGNMENT FIXTURE

The present invention is, therefore, directed to an alignment fixture for the respective lasers which will assure that the corresponding lasers and their beams are preset so that they do accurately impinge and intersect the isocenter 53.

Referring to the drawings, FIGS. 3 through 7, the laser alignment fixture is generally indicated at 55, FIG. 3, and includes the support base 57 having a series of depending equi-angularly spaced adjustable legs 59. Each leg includes a threaded shank 61 to threadedly extend into the undersurface of the support base. Each of the legs includes an enlarged knurled collar 63 to facilitate rotary adjustment of the legs as they rest upon the window 37 as shown in FIGS. 1 and 2.

An adjustment of the legs provides a means of leveling the alignment fixture, utilizing the level 115 upon the turn table 77.

Said support base has a precision machined flat top 65, FIG. 8, a central bore 67 and a counter bore 69.

The bushing 71 of inverted T-shape is projected up into said bore and counter bore with a portion of the bushing of reduced diameter extending above flat top 65 and into a corresponding bore 75 upon the under surface of turntable 77 and secured thereto by the fasteners 79. Said turntable has a precision machined flat bottom 81 for cooperative registry with the corresponding machined flat top 65 of the support base.

The telescope mount 83 is generally rectangular in cross section, has upright side walls and flat top and bottom walls and a longitudinal bore 87. The telescope, generally indicated at 89, FIG. 8, includes the telescope tube 91 which is nested within the bore 87 and includes the wide angle lens system 95 shown. For illustration, the present lens system focuses at approximately forty two inches; namely, at the epicenter axis 25, marking the center of rotation of the gantry 19, FIG. 2.

Said telescope includes the tube extension 97 within tube 91 and terminates in the eyepiece 99 mounting cross hairs 101, FIGS. 4 and 5.

Bushing 71 has a central bore 103 in alignment with the corresponding central bore 105 in turntable 77 providing access to the bottom mirror 109 mounted within a corresponding circular aperture in the bottom surface of telescope mount 83. Mounted upon the telescope mount 83 upon or within the side walls, the top wall and the bottom wall are a series of mirrors designated as bottom mirror 109, top mirror 111 and the side mirrors 113. These are suitably nested and secured within corresponding apertures in the respective walls of the mount. These mirrors are employed in the operation of the alignment fixture for verifying the correct setting and adjustment of the respective lasers as shown in FIG. 1 and in the schematic illustrations 9, 10 and 11.

The level 115 is mounted upon or within the top surface of the turntable 77 as shown in FIG. 6 and includes a graticule 117 and the conventional bubble 119. Accordingly the alignment fixture is leveled by manual adjustment of the respective legs 61.

The present alignment fixture is particularly used by engineers, therapists, installers, and maintenance people for the teletherapy machine shown in FIGS. 1 and 2.

OPERATION

While the present laser alignment fixture has above been described with respect to its use in connection with teletherapy machines, said fixture is adapted for use in conjunction with other devices such as machine tools. For example, the corresponding lasers such as the lasers 41, 45 and 47, may be used upon opposed walls, floor and ceiling, such as shown in FIG. 1 for use in conjunction with a machine tool which has a longitudinal axis, and about which a head is rotatable throughout 360° with the axis of rotation corresponding to the epicenter axis 25 shown in FIG. 2.

Additionally, there may be an operative mechanism connected with the head 21 such as a tool or the like, which is directed radially inward so as to normally intersect the epicenter axis at a point above described as the isocenter.

With such a tool, the present laser alignment device could be used with the corresponding lasers 41 and their beams 43 adjusted so as to impinge upon the point above described as the isocenter such as point 53 of FIG. 1 and, further, that the corresponding lasers 45 and 47 and their respective beams 49 and 51 are adapted to similarly impinge upon said isocenter.

The present laser alignment fixture would be equally applicable for aligning the lasers so that all beams thereof intersect the isocenter as above described.

OPERATION

In operation of the present laser alignment fixture, it becomes necessary to verify that the laser beams are correctly angled and adjusted to assure that they intersect the isocenter. This means that the respective laser beams would lie in a unit plane which extends at right angles to the epicenter axis and intersects the epicenter axis at the isocenter. In order to check the adjustment of the respective lasers the present alignment fixture 55 of FIG. 1 is mounted upon and over the window 37 of platform 35 on the patient couch 33.

As a first step, the gantry is positioned precisely to the vertical position, so that the beam axis is directed vertically downward.

The next step is to position the axis 93 of the telescope at the height of the epicenter 25. This is accomplished by use of an optical distance marking device which usually is built into the treatment machine. Alternatively, an accurate measuring rule is used to set the distance. This latter setting is facilitated by the information always provided by the manufacturer. The distance from the target or source to some accessible external surface is always provided. Thus, if the reference mark is 60 cm from the target or source, and the epicenter is 80 cm from the source, then the telescope axis must be 80 minus 60 or 20 cm from the reference mark. The top surface of mount 83 is precisely 2 cm from the telescope axis. Accordingly, the spacing between the reference mark and the top surface of mount 83 is set at 20 cm minus 2 cm or 18 cm.

As a next step, the alignment fixture is leveled. This is accomplished by such manual adjustment of the respective legs 61 of the support base such that the bubble 119 of the level is central with respect to the corresponding graticule 117 shown in FIG. 6.

As a next step, the telescope is adjusted, if necessary, by rotating table 77 until a sighting through the telescope 89 shows the corresponding cross hairs 101 of the eyepiece 99 in longitudinal alignment and registry with epicenter axis 25 shown as a dot at 25, for example, FIG. 2.

With the alignment device now set up and with the telescope and its longitudinal axis in alignment with the epicenter axis 25, the device is now ready to test the adjusting or focusing of the respective lasers. If the lasers are correctly set, such as shown in FIG. 9, the laser beam 43 will engage the corresponding lateral mirrors 113 and the reflection of the laser beam will coincide with the beam 43 as shown in FIG. 9, indicating that the laser and its beam are correctly set. It is to be kept in mind, furthermore, that the central axes of the mirrors 113, as well as the central axes of the top and bottom mirrors 111 and 109 are in alignment with the longitudinal axis 93 of the telescope.

The same thing is true with respect to the laser 45 which is shown in the ceiling in FIG. 1 but which may, in accordance with the present embodiment, be incorporated into and within the head 21.

The corresponding beam 49, whether it be directed from the laser 45 on the ceiling or within a corresponding laser upon the interior of and coaxial of head 21 will nevertheless impinge upon the top mirror 111 upon the telescope mount shown in FIG. 8.

The arrangement of the apertures within the telescope mount and the side walls and top and bottom walls which receive the respective mirrors are arranged such that the central longitudinal axis of the corresponding mirrors always passes through the longitudinal axis 93 of the telescope.

Accordingly, with all lasers properly adjusted with respect to the laser alignment fixture, and with the fixture in alignment with the epicenter axis as above described, it is then verified that the respective laser beams are each and all passing through the isocenter. Accordingly, once it is known that the laser beams are accurately adjusted when the alignment device is removed and the patient replaces such alignment device, the platform 35 is universally adjusted until the image of the respective laser beams of at least three of the four beams is applied to that designated area of the patient desired to be treated by the high energy beam in the teletherapy machine.

If the lasers 41 are out of adjustment, the beam reflected back from the corresponding mirror will diverge from the main beam 43, such as schematically shown at 44. The image of the reflected beam 44 will show up on the laser housing or the wall as spaced from the laser beam 43 itself, thus, indicating that the laser is out of adjustment. Accordingly, the laser must be adjusted in such a manner that the reflected beam coincides with and registers with the basic laser beam 43 shown in FIG. 9.

The present laser alignment fixture, thus, initially verifies or permits correction of the adjustment of the wall lasers 41 so that the beams 43 thereof are, in effect, impinging upon the isocenter 53.

The floor laser 47 is likewise checked with its beam 51 in registry with the bottom mirror 109, FIG. 8, with access thereto through the central apertures 103 and 105 of bushing 71 and turn table 77. By the same procedure, the reflected beam corresponding to the laser beam 49 must be in registry with and in impingement upon the source of such beam in the same manner as shown in FIG. 9 to verify that the beam is passing through the isocenter.

It therefore can be safely concluded that when the designated area on the patient to be treated is impinged upon by the respective laser beams or at least three of the four, then it is known and verified that the platform has been correctly adjusted and the patient located so that the high energy beam from the linear accelerator throughout all positions of rotation of the gantry 19 around epicenter axis 25 will impinge upon the predesignated area of the patient's body to be treated.

Having described my invention, reference should now be had to the following claims.

I claim:

1. An alignment fixture particularly for alignment of high energy sources including lasers, comprising a centrally apertured support base mountable upon a support;
  a centrally apertured turntable mounted and journalled upon said support base;
  a telescope mount on and secured to said turntable having side walls, top and bottom walls and a longitudinal bore;
  a telescope supported within said bore having a longitudinal axis, and an eyepiece with cross hairs, said support base being adjustably mounted whereby said cross hairs are adapted for visible alignment with the epicenter axis of rotation of a teletherapy machine head; said head adapted to direct a radial high energy beam at right angles to and intersecting said epicenter axis at an isocenter;
  and a mirror mounted on each of said telescope mount walls, with their central axes passing through said longitudinal axis;
  said mirrors being adapted to reflect the beams of a series of right-angularly related pairs of opposed light sources spaced therefrom to verify by the reflection of said beams upon said mirrors with the respective beams all intersecting said isocenter.

2. In the alignment fixture of claim 1, an upwardly directed level mounted on said turn table including cross hairs to facilitate leveling of said turn table.

3. In the alignment fixture of claim 1, the mounting and journalling of said turn table including a centrally apertured bushing of inverted T-shape in cross section nested within a similarly shaped undercut bore in and retainingly engaging said support base, and projecting above said support base into a corresponding counterbore in the undersurface of said turn table; and fasteners interconnecting said bushing and turn table.

4. In the alignment fixture of claim 1, there being circular recesses in the walls of said telescope mount receiving said mirrors.

5. In the alignment fixture of claim 1, the mounting of said support base upon said platform including a plurality of spaced, longitudinally adjustable legs threaded into and depending from said support base.

6. In the alignment fixture of claim 5, there being three equidistant legs adjacent the periphery of said support base.

7. In the alignment fixture of claim 5, there being an enlarged knurled circular collar upon each leg to facilitate rotary adjustment thereof.

8. For use in conjunction with a teletherapy machine in a room and having a head supporting gantry mounted for rotation about an epicenter axis; and right-angularly related coplaner pairs of spaced opposed lasers adjustably mounted upon the room walls, the floor and above the epicenter axis, said head in all rotated positions of said gantry adapted to direct a radial high energy beam at right angles to and intersecting said epicenter axis at the isocenter, within the plane of beams of said lasers, said lasers being adjusted so that their beams intersect at said isocenter, there being a patient couch within said room having a universally adjustable platform spaced from said head with a window in said platform;
  a laser alignment fixture comprising a centrally apertured support base mounted on said window;
  a centrally-apertured turntable mounted and journalled upon said base;
  a telescope mount on said turntable having side walls, top and bottom walls, and a longitudinal bore;
  a telescope mounted within said bore having a longitudinal axis and an eyepiece with cross hairs;
  said support base being adjustably positioned by said platform whereby said cross hairs are visibly alignable with said epicenter axis;
  and a mirror secured on each of said telescope mount walls, with their central axes passing through said longitudinal axis;
  said mirrors being spaced from and opposed to each of said lasers respectively whereby, when the lasers are correctly adjusted so that the respective laser beams impinge on said isocenter, the respective beams reflected by said mirrors will coincide visibly with the corresponding laser beams.

9. In the laser alignment fixture of claim 8, the laser above the epicenter axis being disposed within the machine head.

10. In the laser alignment fixture of claim 8, the laser above the epicenter axis being mounted upon the room ceiling.

11. In the laser alignment fixture of claim 8, the lasers having a universal mounting for linear and angular adjustment of their beams.

12. In the laser alignment fixture of claim 8, when the respective laser beams are adjusted to register with said isocenter, and said isocenter corresponds to the localized area of a patient of said platform to be treated, it is predetermined that upon all rotational positions of adjustment of said machine head about said epicenter axis, all energy beams from said head will pass through said localized area.

13. In the laser alignment fixture of claim 8, the apertures in said support base and turn table being in alignment with the axes of the mirror upon the bottom wall of said telescope mount and the floor-mounted laser.

14. In the laser alignment fixture of claim 8, said couch platform being adjustable vertically, laterally and longitudinally, whereby with a patient lying upon said platform, the patient may be so moved that a designated area on the patient for treatment is positioned with at least three laser beams impinging upon said designated area to assure the said designated area to assure the said designated area is located at said isocenter.

15. In the laser alignment device of claim 8, said support base having a flat top with a precision-machined surface; said turntable having a flat bottom with a precision-machined surface.

16. In the laser alignment fixture of claim 8, there being aligned pairs of circular recesses in the walls of said telescope mount receiving said mirrors.

17. In the laser alignment fixture of claim 8, the mounting and journalling of said turntable including a centrally apertured bushing of inverted T-shape in cross section nested within a similarly shaped undercut bore in and retainingly engaging said support base, and projecting above said support base into a corresponding counter bore in the undersurface of said turntable; and fasteners interconnecting said bushing and turntable.

18. In the laser alignment fixture of claim 17, fasteners interconnecting said turntable and telescope mount.

19. In the laser alignment fixture of claim 8, the mounting of said support base on said platform window including a plurality of spaced longitudinally adjustable legs threaded into and depending from said support base.

20. In the laser alignment fixture of claim 19, there being three equidistant legs adjacent the periphery of said support base.

21. In the laser alignment fixture of claim 19, there being an enlarged knurled circular collar upon each leg to facilitate rotary adjustment thereof.

22. In the laser alignment fixture of claim 19, an upwardly directed level mounted upon said turntable including cross hairs to facilitate leveling of said turn table.

23. In a teletherapy machine disposed in a room and having a head supporting gantry mounted for rotation about an epicenter axis; and right-angularly related coplaner pairs of spaced opposed lasers adjustably mounted upon the room walls, the floor and above the epicenter axis, said head in all rotated positions of said gantry adapted to direct a radial high energy beam at right angles to and intersecting said epicenter axis at the isocenter, within the plane of beams of said lasers, said lasers being adjusted so that their beams intersect at said isocenter, there being a patient couch within said room having a universally adjustable platform spaced from said head with a window in said platform;

the improvement including a laser alignment fixture comprising a centrally apertured support base mounted on said window;

a centrally apertured turntable mounted and journalled upon said support base;

a telescope mount on said turntable having side walls, top and bottom walls, and a longitudinal bore;

a telescope supported within said bore having a longitudinal axis, and an eyepiece with cross hairs, said support base being adjustably positioned by said platform whereby said cross hairs are visibly alignable with said epicenter axis;

and a mirror mounted on each of said telescope mount walls, with their central axes passing through said longitudinal axis;

said mirrors being spaced from and opposed to each of said lasers respectively whereby, when the lasers are correctly adjusted so that the respective laser beams impinge on said isocenter, the respective beams reflected by said mirrors will coincide visibly with the corresponding laser beam.

24. In a room with floor, walls and ceiling adapted to enclose a teletherapy machine, said machine having a head supporting gantry mounted for rotation about a horizontal epicenter axis; said head adapted to direct a radial high energy beam at right angles to and intersecting said epicenter axis at the isocenter, there being a patient couch in said room having a universally adjustable platform spaced from said head with a window in said platform, a first pair of spaced lasers respectively mounted on a pair of opposed walls, a laser mounted on said floor, and a laser spaced from and opposed to the floor laser mounted in said room above said epicenter axis, said lasers lying in a plane extending at right angles to said epicenter axis, and passing through said isocenter, said lasers being so adjusted that their respective beams are adapted to intersect said isocenter;

the improvement comprising an alignment fixture for said lasers comprising a centrally apertured support base mounted on said window;

a centrally apertured turntable mounted and journalled upon said support base;

a telescope mount on said turntable having side walls, top and bottom walls, and a longitudinal bore;

a telescope supported within said bore having a longitudinal axis and an eyepiece with cross hairs;

said support base being adjustably positioned by said platform whereby said cross hairs are visibly alignable with said epicenter axis; and a mirror mounted on each of said telescope mount walls, with their central axes passing through said longitudinal axis;

said mirrors being spaced from and opposed to each of said lasers respectively whereby, when the lasers are correctly adjusted so that the respective laser beams impinge on said isocenter, the respective beams reflected by said mirrors will coincide visibly with the corresponding laser beam.

25. In a room with floor, walls and ceiling adapted to enclose a teletherapy machine having a head mounted for rotation about a horizontal epicenter axis, said head adapted to direct a radial high energy beam at right angles to and intersecting said epicenter axis at an isocenter, a universally adjustable platform on said floor spaced from said head, and opposed right angularly related pairs of lasers mounted on a pair of walls, said floor and above said epicenter axis, said lasers being so adjusted that their beams are coplaner and intersect said isocenter;

the improvement including an alignment fixture for said lasers comprising a centrally apertured support base mounted on said platform;

a centrally apertured turntable mounted and journalled upon said support base;

a telescope mount on said turntable having side walls, top and bottom walls, and a longitudinal bore;

a telescope supported within said bore having a longitudinal axis, and an eyepiece with cross hairs, said support being adjustably positioned by said platform whereby said cross hairs are visibly alignable with said epicenter axis;

and a mirror mounted on each of said telescope mount walls, with their central axes passing through said longitudinal axis;

said mirrors being spaced from and opposed to each of said lasers respectively, whereby when the lasers are correctly adjusted so that the respective laser beams impinge on said isocenter, the respective beams reflected by said mirrors will coincide visibly with the corresponding laser beam.

26. In a room with floor, walls and ceiling adapted to enclose a machine tool, said machine tool having a head supporting gantry mounted for rotation about a longitudinal epicenter axis, said head mounting a tool which extends at right angles to and intersects said epicenter axis at an isocenter, there being a manually adjustable support on said floor spaced from said head;

a first pair of spaced opposed lasers respectively mounted on a pair of opposed walls, and a laser mounted upon said ceiling, said lasers lying in a plane extending at right angles to said epicenter axis and passing through said isocenter;

said lasers being so adjusted that their respective beams are adapted to intersect said isocenter;

the improvement comprising an alignment fixture for said lasers comprising a centrally apertured support base mounted on said adjustable support;

a centrally apertured turn table mounted and journalled upon said support base;

a telescope mount on said turn table having side walls, top and bottom walls and a longitudinal bore;

a telescope supported within said bore and having a longitudinal axis, with an eyepiece with cross hairs, said support base being adjustably mounted whereby said cross hairs are visibly alignable with said epicenter axis;

and mirrors mounted upon the telescope mount side walls and upon the top thereof, with their central axes passing through said longitudinal axis;

said mirrors being spaced from and opposed to each of said lasers respectively, whereby when the lasers are correctly adjusted so that the respective laser beams impinge on said isocenter, the respective beams reflected by said mirrors will coincide visibly with the corresponding laser beam.

27. In a room with floor, walls and ceiling adapted to enclose a teletherapy machine having a head mounted for rotation about a horizontal epicenter axis, said head adapted to direct a radial high energy beam at right angles to and intersecting said epicenter axis at an isocenter;

an adjustable platform on said floor spaced from said head;

an opposed pair of lasers mounted on a pair of opposed walls and a further laser mounted above said epicenter axis;

said lasers so located that their beams are coplaner and intersect said isocenter;

the improvement consisting of a laser alignment fixture comprising a support base mounted on said platform;

a turntable mounted and journalled upon said support base;

a telescope mount on said turntable having side walls, top and bottom walls and a longitudinal bore;

a telescope supported within said bore having a longitudinal axis and an eyepiece with cross hairs, said support base being adjustable whereby said cross hairs are visibly in alignment with said epicenter axis;

mirrors mounted upon the side walls of said telescope mount and upon the top wall thereof, with their central axes passing through said longitudinal axis;

said mirrors being spaced from and opposed to each of said lasers respectively, whereby when the lasers are correctly adjusted so that the respective laser beams impinge on said isocenter, the respective reflected beams will coincide visibly with the corresponding laser beam.

* * * * *